United States Patent [19]

Gyory et al.

[11] Patent Number: 5,162,042

[45] Date of Patent: Nov. 10, 1992

[54] ELECTROTRANSPORT TRANSDERMAL SYSTEM

[75] Inventors: J. Richard Gyory, Los Altos; Ronald P. Haak, Cupertino; Felix Theeuwes, Los Altos, all of Calif.

[73] Assignee: ALZA Corporation, Palo Alto, Calif.

[21] Appl. No.: 815,558

[22] Filed: Dec. 27, 1991

Related U.S. Application Data

[63] Continuation of Ser. No. 600,284, Oct. 17, 1990, abandoned, which is a continuation of Ser. No. 215,150, Jul. 5, 1988, abandoned.

[51] Int. Cl.$^5$ ............................................. A61N 1/30
[52] U.S. Cl. ................................... 604/20; 128/798; 128/802
[58] Field of Search .................. 604/20; 128/798, 802, 128/803

[56] References Cited

U.S. PATENT DOCUMENTS

| | | | |
|---|---|---|---|
| 116,562 | 7/1871 | Collins | 604/20 |
| 175,974 | 4/1876 | Hall | 128/390 |
| 393,741 | 12/1888 | Collins | 128/390 |
| 3,982,529 | 9/1976 | Sato | 128/641 |
| 4,211,222 | 7/1980 | Tapper | 128/803 |
| 4,274,420 | 6/1981 | Hymes | 128/641 |
| 4,325,367 | 4/1982 | Tapper | 128/207.21 |
| 4,383,529 | 5/1983 | Webster | 604/20 |
| 4,419,092 | 12/1983 | Jacobsen et al. | 604/20 |
| 4,457,748 | 7/1984 | Lattin et al. | 604/20 |
| 4,474,570 | 10/1984 | Ariura et al. | 604/20 |
| 4,557,723 | 12/1985 | Sibalis | 604/20 |
| 4,570,637 | 2/1986 | Gomes et al. | 128/803 |
| 4,622,031 | 11/1986 | Sibalis | 604/20 |
| 4,640,689 | 2/1987 | Sibalis | 604/20 |
| 4,702,732 | 10/1987 | Powers et al. | 604/20 |
| 4,708,716 | 11/1987 | Sibalis | 604/20 |
| 4,713,050 | 12/1987 | Sibalis | 604/20 |
| 4,722,726 | 2/1988 | Sanderson et al. | 604/20 |
| 4,725,263 | 2/1988 | McNichols et al. | 128/803 |
| 4,731,926 | 3/1988 | Sibalis | 29/877 |
| 4,734,090 | 3/1988 | Sibalis | 128/798 |
| 4,747,819 | 5/1988 | Phipps et al. | 604/20 |
| 4,752,285 | 6/1988 | Petecenz et al. | 604/20 |
| 4,808,152 | 2/1989 | Sibalis | 604/20 |
| 4,849,226 | 7/1989 | Gale | 604/890.1 |
| 4,927,408 | 5/1990 | Haak et al. | 604/20 |

FOREIGN PATENT DOCUMENTS

| | | | |
|---|---|---|---|
| 3020789 | 1/1982 | Fed. Rep. of Germany | 604/20 |
| 410009 | 5/1934 | United Kingdom | 604/20 |

OTHER PUBLICATIONS

P. Tyle & B. Kari, "Iontophoretic Devices," in Drug Delivery Devices, pp. 421–454 (1988).

*Primary Examiner*—Stephen C. Pellegrino
*Assistant Examiner*—Michael Rafa
*Attorney, Agent, or Firm*—D. Byron Miller; Edward L. Mandell; Steven F. Stone

[57] ABSTRACT

A transdermal therapeutic system which utilizes electrical current to facilitate drug delivery.

18 Claims, 5 Drawing Sheets

ELECTROTRANSPORT TRANSDERMAL SYSTEM

This application is a continuation of application Ser. No. 600,284, filed Oct. 17, 1990, abandoned, which application is a continuation of Ser. No. 215,150, filed Jul. 5, 1988, abandoned.

FIELD OF THE INVENTION

This invention relates to transdermal drug delivery. More particularly, this invention relates to transdermal drug delivery systems capable of delivering drugs or dose regimens not otherwise suitable for passive drug delivery. Still more particularly, but without limitation thereto, this invention relates to transdermal systems which utilize electrical current to facilitate drug delivery.

BACKGROUND OF THE INVENTION

Many drugs are not suitable for passive drug delivery because of their size, ionic charge characteristics and hydrophilicity. One method of overcoming this limitation in order to achieve transdermal administration of such drugs is the use of electrical current to actively transport drugs into the body, as for example, through intact skin. This concept is based upon basic principles of electrochemistry and is defined as electrically assisted transport, hereinafter referred to as "electrotransport". An electrochemical cell in its simplest form consists of two electrodes and associated half cell reactions, between which electrical current can flow. Electrical current flowing through the metal portion of the circuit is carried by electrons (electronic conduction), while current flowing through the liquid phase is carried by ions (ionic conduction). In order for current to flow in an electrochemical cell, it is necessary for electrical charge to be transferred to chemical species in solution by means of oxidation and reduction charge transfer reactions at the electrode surfaces.

As electrical current flows, oxidation and reduction of some chemical species take place. A variety of electrochemical reactions can be utilized, and these fall into two classes. In one class, the electrode material participates in the charge transfer reaction; i.e., the electrode material is consumed or generated. In the other class, the electrode material behaves as a catalyst; i.e., the reduced and oxidized species exist in solution and the charge transfer reaction is catalyzed at the electrode surface. An example of the former is represented by:

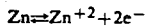

or

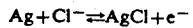

where the forward reaction is the oxidation or anodic process and the reverse reaction is the reduction or cathodic process.

Examples of electrochemical reactions involving species independent of the electrode materials are the hydroquinone/quinone and the ferrous/ferric ion couples:

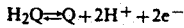
and

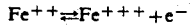

Again, the forward reaction is the anodic process and the reverse reaction is cathodic. These reactions are catalyzed by an appropriate conducting surface When electrical charge is either generated or consumed at an electrode surface, ionic species must be transported to maintain electroneutrality throughout the system. Three physical processes contribute to this transport: passive diffusion, electromigration and convection.

The Nernst-Planck equation (1) expresses the flux for any particular chemical species, i, in the presence of an electrical field. The development of this equation is well known and explained in detail in electrochemistry texts such as J.S.Newman, Electrochemical Systems (Prentice-Hall, 1973) and A.J.Bard & L.R.Faulkner, Electrochemical Methods, Fundamentals and Applications (John Wiley & Sons, 1980). Therefore, only pertinent conclusions will be presented here.

The Nerst-Planck equation (1) has three terms, one for each of the physical processes contributing to the mass transport. The first term describes the flux due to passive diffusion, which is proportional to the concentration gradient of species i. The second term describes the flux due to electromigration or electrodiffusion, where the driving force is the gradient of electrical potential. The third term describes the flux due to convection, where the mechanism of transport is the movement of material by bulk fluid flow which is determined by the magnitude and direction of the bulk fluid velocity vector.

$$J_i = -D_i \nabla C_i - z_i F u_i C_i \nabla \Phi + C_i v \quad (1)$$

where
- $J_i$ = flux of species i (moles/cm$^2$-sec)
- $D_i$ = diffusion coefficient of i (cm$^2$/sec)
- $\nabla$ = the gradient operator
- $C_i$ = concentration of i
- $z_i$ = number of charges per molecule of i
- F = Faraday's constant (96,500 coulombs/mole of charge)
- $u_i$ = mobility of i (velocity/force)
- $\Phi$ = electrical potential (volts)
- v = velocity vector Considering transport in only one direction of a rectilinear coordinate system, equation (1) may be simplified to:

$$J_{i,x} = -(D_i)(dC_i/dx) + z_i F u_i C_i E_x + C_i v_x \quad (2)$$

where
- $J_{i,x}$ = flux of species i in the x direction
- $E_x$ = electrical field in the x direction; i.e., the negative of the electrical potential gradient
- $v_x$ = the x component of the velocity vector When an electrochemical half cell containing one or more drug species is placed upon the skin (the positive x-direction being perpendicular to the skin and directed out of the device and into the body), a concentration gradient will be established across the skin by virtue of the fact that the device contains a finite concentration of drug species and presumably, at least initially, the body contains a lower concentration of the species. Therefore, transport of material by passive diffusion will proceed.

If another electrode, electrically connected to the first electrode is placed on the skin, an electrical field may be imposed across the skin by applying a potential difference between these two electrodes. If the drug species exist in solution as charged species, then transport of material will proceed by electromigration. Additionally, a bulk fluid flow can exist with a net transfer of material from the patch into the body, when an electrical field is imposed across the skin. This process, called electroosmosis, can also result in the net flux of drug species from the patch into the body.

Equation (2) applies within each and every phase and the physical constants and extensive properties must be applicable to the phase of interest. In this manner, one form of equation (2) holds within the electrotransport patch where $D_i$, $C_i$, $u_i$ and so forth, are the diffusion coefficient, concentration, and mobility of species i within the patch materials. In the skin, another identical form of equation (2) holds except the diffusion coefficient, concentration and mobility of species i are now those within the skin. The extensive properties of these equations, such as the concentration and electric field, are linked at the interface by proportionality constants such as the partition coefficient and the ratio of dielectric constants, respectively.

As described above, three physical processes may contribute to the mass transport of a particular chemical species across the skin when an electrical field is imposed across the skin. It is the sum of the fluxes resulting from these three processes, passive diffusion, electromigration and bulk fluid flow resulting from electroosmosis, which define electrotransport.

Electrotransport is ideal for controlled delivery of substances having relatively low passive diffusion transport rates. In that instance, the first term of equation (1) would be very small in comparison to the second electromigration and/or third convective (electroosmotic) terms. For such a substance, drug delivery can be controlled by the electrical current applied through the patch.

When current is passed between two electrodes placed on the skin, the charge carriers through the skin and body are ions; for example, the ionized drug and endogenous ions such as sodium, potassium, and chloride ions. The total current density, i, is the sum of the current densities carried by each charged species, $i_j$, as is shown by the following equation:

$$i = \sum_j i_j = \sum_j |z_j| F u_j C_j E \qquad (3)$$

where E is the magnitude of the electrical field. The fraction of current carried by any particular species is given by the ratio of $i_j$ to i and this ratio, $t_j$, is called the transference number of species j and is expressed as:

$$t_j = i_j/i = (|z_j| u_j C_j)/(\Sigma |z_k| u_k C_k) \qquad (4)$$

The transference number indicates the fraction of the current carried by the drug ion in the skin. This is the most difficult factor to predict because it depends upon many physical, chemical and biological factors; for example, the total concentration of drug and its mobility in the skin, the local pH that determines the fraction of ionized drug, and the mobilities and concentrations of other ions.

An electric field not only gives rise to electromigration, it can also induce an electroosmotic flow. Electroosmosis is defined as the volume flow of solvent through a charged membrane when an electrical field is imposed across that membrane. The skin itself behaves as a charged membrane with its isoelectric point being within the range of about $pH_{iso}$ of 4.0–5.5, meaning that the skin is positively charged below this point and negatively charged above. When solvent is transported, charged or uncharged solutes contained therein may also be transported, including macromolecules and polypeptides. In this manner, electroosmosis can be used for the transdermal transport of neutral, as well as charged compounds.

The electroosmotic flow is generated by electromigration of ions which exist in the diffuse double layer next to the surface of a charged membrane. These ions entrain bulk solvent resulting in a flow. Equation (5) shows that the average velocity, $<v>$, through a pore is proportional to the total current, I, flowing through that pore:

$$<v> = (\epsilon \zeta I)/(\kappa \mu) \qquad (5)$$

where
- $\epsilon$ = electrical permitivity in the fluid phase
- $\zeta$ = zeta potential of the membrane
- $\kappa$ = conductivity of the fluid phase
- $\mu$ = viscosity of the fluid phase Equations (1) through (5) demonstrate that when passive diffusion is a minor component to the flux of a species and when the only convective flux is that resulting from electroosmosis, the flux of any particular species is directly proportional to the current density. Therefore, under these conditions control of the current density can be used to control the flux of drug through skin.

In applying these principles to drug delivery, the drug being delivered can be electrically assisted into the skin. There are a number of categories in which drug delivery systems utilizing electrotransport principles can offer major therapeutic advantages. See P.Tyle & B.Kari, "Iontophoretic Devices", in DRUG DELIVERY DEVICES, pp. 421–454 (1988).

Even though the concept of electrotransport in drug delivery is known, there is a continuing need to develop systems with improved control of the drug delivery rate, along with overcoming problems associated with known electrotransport devices, such as size, reliability, comfort to the wearer, composition and programmability.

SUMMARY OF THE INVENTION

An object of this invention is to provide an improved approach and device for the controlled and sustained transdermal transport of drugs.

Another object of this invention is to provide for electrically assisted transdermal delivery of drugs, and also to provide for enhanced drug transport at rates higher than those achieved by passive diffusion.

A further object of this invention is to optimize system components and processes including electrochemical reactions, electrolyte compositions and the electrical power supply.

A still further object of this invention is to provide an electrotransport transdermal drug delivery system with a minimal power requirement.

Another object of this invention is to provide programmable drug delivery.

An even further object of this invention is to provide electrically assisted delivery systems capable of delivering macromolecules, peptides and polypeptides.

These and other objects, features and advantages of the invention have been demonstrated by the present invention wherein a self contained electrotransport transdermal system for placement on a body surface is comprised of: a non-conductive backing member; a source of electrical power comprising first and second current conducting members, said current conducting members being positioned adjacent to said backing member and either in direct contact with each other so as to form a galvanic couple or positioned in direct contact with opposite poles of a power supply such as a battery; a first electrode pad containing an agent to be delivered, positioned adjacent to said first current conducting member and positioned in current conducting relationship to said body surface; a second electrode pad positioned on the body in relationship to said second current conducting member and positioned in current conducting relationship to said body surface; an optional insulating means, insulating said first and said second electrode pads from each other; and a means for maintaining said system in current conducting and agent transmitting relationship to said body surface.

BRIEF DESCRIPTION OF THE DRAWING

The invention will be described in further detail with reference to the accompanying drawings wherein.

DESCRIPTION OF THE INVENTION

Figure 1:
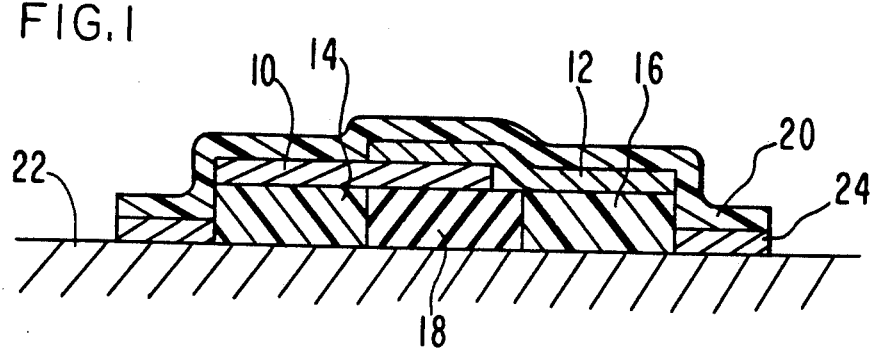
FIG. 1 is a schematic cross sectional view of one embodiment of the electrotransport transdermal therapeutic system of this invention having a peripheral adhesive layer, where electrical power is supplied by a galvanic couple.

This invention is best described with reference to the accompanying drawings. In general terms, this invention, of which FIG. 1 is a typical example, is an electrotransport transdermal system having two current conducting members, referred to herein as a donor electrode 10 and a counter electrode 12, each electrode being positioned adjacent to the donor electrode pad 14 and counter electrode pad 16, respectively. The pads are separated by an insulator 18. The system has a backing layer 20 made of an electrically insulating or non-conductive material such as is commonly used in transdermal systems The system adheres to the skin 22 by means of a peripheral adhesive layer 24. Suitable adhesives include, without limitation, polyisobutylene/mineral oil and silicone adhesives. The system would normally include a strippable release liner, not shown.

It is believed that this invention has utility in connection with the delivery of drugs within the broad class normally delivered through body surfaces and membranes, including skin. As used herein, the expressions "agent" and "drug" are used interchangeable and are intended to have their broadest interpretation as any therapeutically active substance which is delivered to a living organism to produce a desired, usually beneficial, effect. In general, this includes therapeutic agents in all of the major therapeutic areas including, but not limited to, anti-infectives such as antibiotics and antiviral agents, analgesics and analgesic combinations, anesthetics, anorexics, antiarthritics, antiasthmatic agents, anticonvulsants, antidepressants, antidiabetic agents, antidiarrheals, antihistamines, anti-inflammatory agents, antimigraine preparations, antimotion sickness preparations, antinauseants, antineoplastics, antiparkinsonism drugs, antipruritics, antipsychotics, antipyretics, antispasmodics, including gastrointestinal and urinary, anticholinergics, sympathomimetrics, xanthine derivatives, cardiovascular preparations including calcium channel blockers, beta-blockers, antiarrythmics, antihypertensives, diuretics, vasodilators, including general, coronary, peripheral and cerebral, central nervous system stimulants, cough and cold preparations, decongestants, diagnostics, hormones, hypnotics, immunosuppressives, muscle relaxants, parasympatholytics, parasympathomimetrics, proteins, peptides, psychostimulants, sedatives and tranquilizers The size of the electrotransport transdermal system of this invention can vary from less than 1 cm$^2$ to greater than 200 cm$^2$. The average system however, will have a size within the range of about 5-50 cm$^2$.

Figure 2:
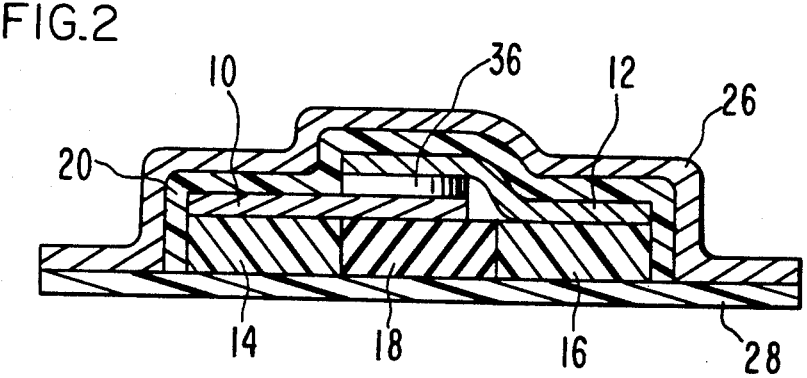
FIG. 2 is a schematic cross sectional view of an embodiment of this invention having an adhesive overlay and an integral power source.

FIG. 2 is an embodiment illustrating use of an adhesive overlay 26. This is advantageous when the ions flowing out of or into the electrode pads may be incompatible with the adhesive material. The system is also illustrated with a strippable release liner 28.

Figure 3:
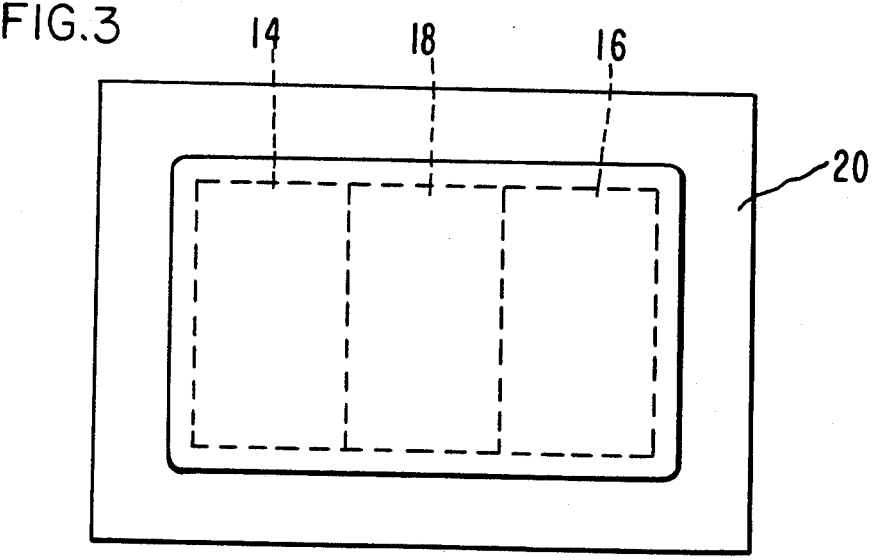
FIG. 3 is a top view of the embodiments of FIGS. 1 and 2.

FIGS. 1 and 2 illustrate parallel alignment of the counter and donor electrodes and pads, as is shown by the top view in FIG. 3.

Figure 4:
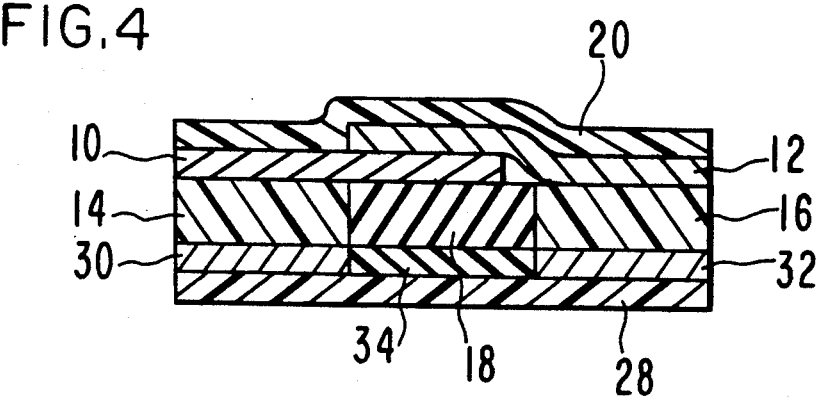
FIG. 4 is a schematic cross sectional view of an embodiment of the invention having an in-line ion conducting contact adhesive.

FIG. 4 is another embodiment of the invention, where the adhesive is positioned between the skin and the electrode pads 14 and 16. In order to allow the system to transfer components to and from the skin, the adhesive must be ion conducting. To avoid transference of ions across the skin surface, the adhesive 30 under the donor electrode pad 14 is separated from the adhesive 32 under the counter electrode pad 16 by a barrier 34, such as an air gap, a non-ion conducting adhesive (hydrophobic) or other suitable barrier to ion flow.

Figure 5:
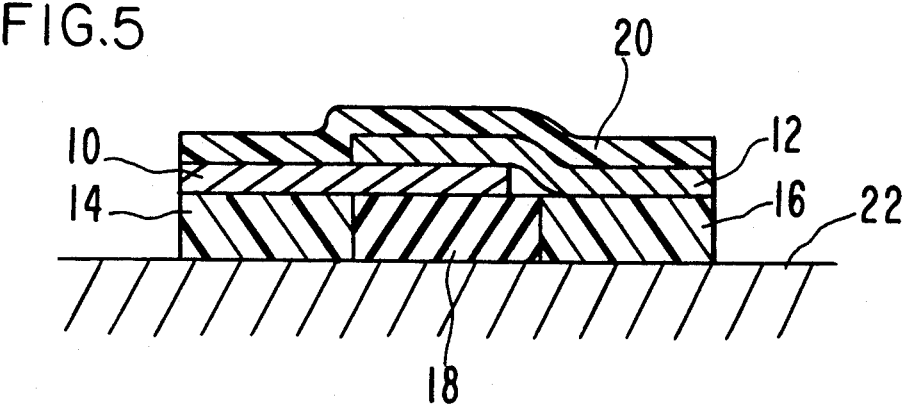
FIG. 5 is a schematic cross sectional view of an embodiment of the invention having a self-adhering matrix.
Figure 6:
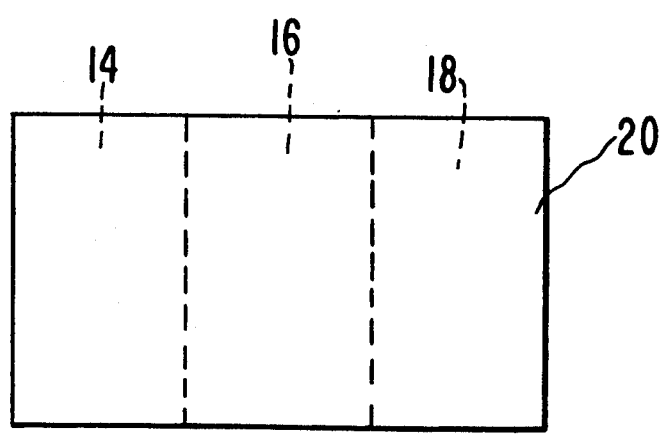
FIG. 6 is a top view of the embodiments of FIGS. 4 and 5.

FIG. 5 illustrates a system where pads 14 and 16 are self-adhering matrices. FIG. 6 provides a top view which illustrates that this embodiment provides for parallel alignment of the donor and counter electrode pads.

Figure 7:
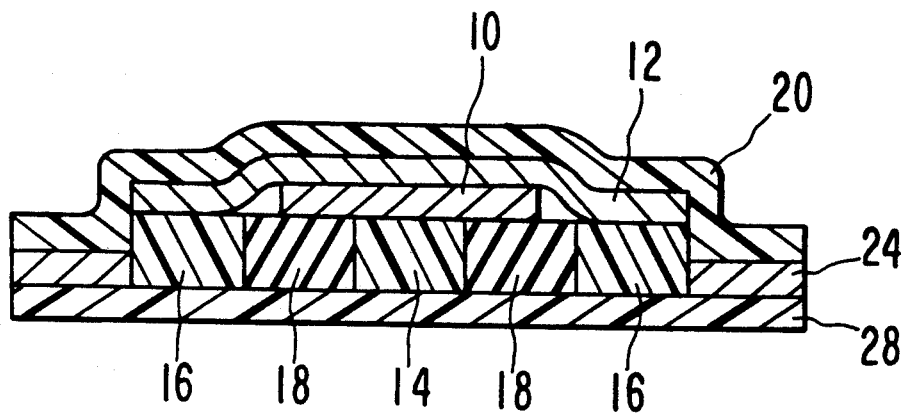
FIG. 7 is a schematic cross sectional view of another embodiment of this invention where the donor electrode is surrounded at its periphery by the counter electrode.
Figure 8:
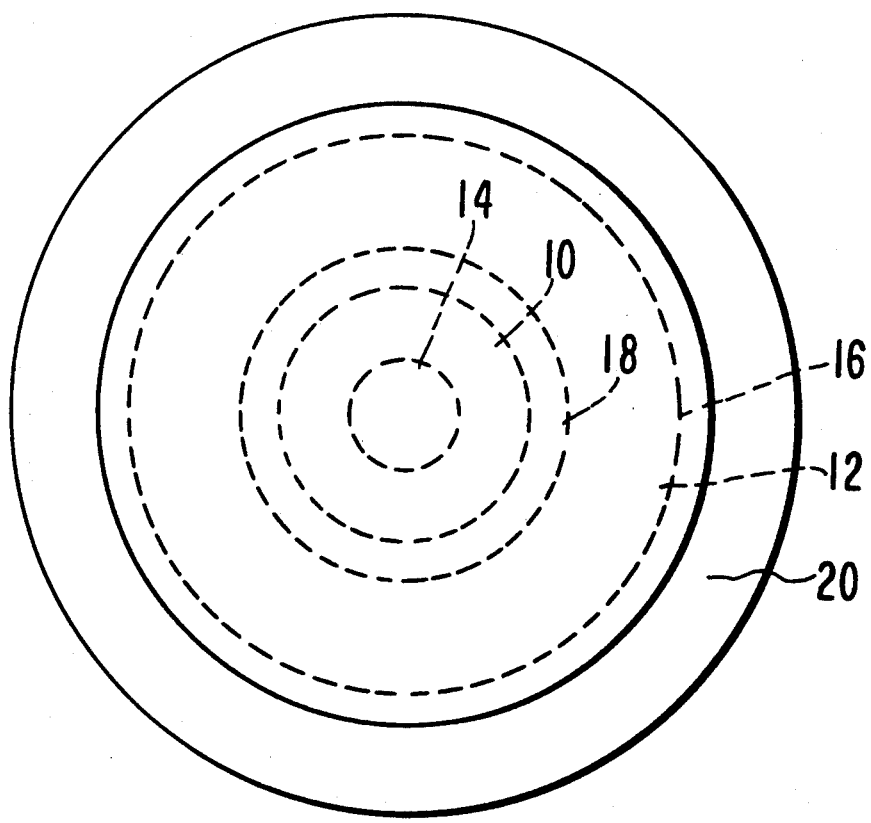
FIG. 8 is a top view of the embodiment of FIG. 7.

In an alternate design, the electrodes can be aligned peripherally. This is shown in FIG. 7 where the donor electrode pad 14 is in the center, surrounded by an insulator 18 and the counter electrode pad 16. The electrode pads can also be reversed with the donor electrode pad on the exterior and the counter electrode pad in the center, if desired. The peripheral alignment can be circular as is shown by the top view in FIG. 8. However, this invention is not limited to that configuration and can be, for example, elliptical, rectangular or any of a variety of geometric configurations.

Transport of species during the passage of electrical current is accomplished via the following mechanisms: passive diffusion, electromigration and electroosmosis. The latter two electrokinetic processes are of the greatest concern, since the object of this invention is to use electrical current to enhance the transdermal transport obtained by passive diffusion alone. For purposes of illustration only, the drug being delivered shall be referred to as being positively charged. It is to be understood however, that both negatively charged and neutral drug molecules can also be delivered by the electrotransport systems of this invention.

Further, for illustration purposes only, the donor electrode pad 14 shall be described as containing the drug to be delivered and the counter electrode pad 16 shall be described as containing a cation-anion pair. This invention does however, contemplate placing drug in both electrode pads and in that manner both pads would function as donor electrode pads. For example, positive ions could be introduced into tissues from the anode (positive electrode), while negative ions could be introduced from the cathode (negative pole). Alternatively, neutral drugs can be introduced from either electrode by electroosmosis.

The embodiment of FIG. 1 is a galvanic couple formed by the donor 10 and counter 12 electrodes, which for a positively charged drug are the anode and cathode, respectively. When the system is in storage no current flows because the circuit is not closed. The circuit is closed when the system is placed on the skin 22, the body acting as an ion-conducting pathway, as is shown in FIG. 1.

Power Supply

The electrotransport transdermal system of this invention can operate in numerous ways, depending upon the requirements of the system.

If the counter and donor electrodes are of dissimilar metals or have different half cell reactions, it is possible for the system to generate its own electrical power. This embodiment is shown in FIG. 1 where the electrodes 10 and 12 are positioned adjacent to each other and to their respective electrode pads. Typical materials to provide such a galvanic couple include using a zinc donor electrode 10 and a silver/silver chloride counter electrode 12. Such a combination can provide about 1 volt.

In this instance, the donor electrode pad 14 is an integral part of the power generating process. The system activates automatically when applied to intact skin because at that time the electrical conduction circuit is closed and drug transport is initiated.

In some instances it may be necessary to augment the power supplied by the galvanic electrode couple. This can be accomplished by placement of a separate power source 36, such as a battery or series of batteries, positioned between the donor electrode 10 and the counter electrode 12 as is shown in FIG. 2, such that electrode 10 is in direct contact with one pole of the power supply and electrode 12 is in direct contact with the opposite pole.

The selection of electrochemical reactions for use in electrotransport systems are governed by various considerations including: the thermodynamics and kinetics of the reactions; the effect the reactants and products have on the electrolyte composition, for example, the pH and ionic strength; the compatibility of the electrode materials, reactants and products with other cell components, for example, the drug species; and the biocompatibility of the reactants and the products.

Standard electrochemical reactions and the respective reduction potentials are well known in the art. See the CRC Handbook of Chemistry and Physics, pp. D 151-158, 67th edition (1986-1987). Proper selection of the components and electrochemical reactions for the anode and cathode can allow the transdermal electrotransport system to function as its own battery. For example, use of the following reaction at the anode:

$$Zn \rightarrow Zn^{+2} + 2e^-$$

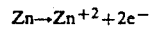

$E_{oxidation} = 0.763$ volts and the following reaction at the cathode:

$$O_2 + 4H^+ + 4e^- \rightarrow 2H_2O$$

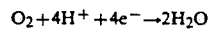

$E_{reduction}$ at pH 4 = 0.997 volts a cell voltage of about 1.76 volts (0.763 + 0.997) at a pH of 4, can be obtained. If the average skin resistance is about 10 kohms-cm$^2$ (R) and the skin resistance is the predominant impedance component, then a current of about 85 $\mu$A/cm$^2$ could be achieved without the use of an external power supply. This is based on the resistance of two skin layers and it is assumed that there is negligible resistance within the donor and counter electrode pads.

This is all based upon Ohm's Law which states that:

$$V = (I)(R)$$

where
V = voltage
I = current
R = resistance

The resistance as noted above, is primarily that of the skin. A desired current density is established and from those values, the voltage requirements of the system can be determined.

In addition to the thermodynamics of the electrochemical reactions, the kinetics of the processes must be considered. The primary concern is that the reaction can proceed at a rate sufficient to maintain the desired current. If the reaction kinetics are too slow, other reactions will occur and could introduce contaminants which are detrimental to the overall electrotransport process, for example by changing the pH of the electrolyte. One measure of the kinetics of a reaction is the reversibility of the reaction. For the present applications, it is important to insure that the kinetics of a reaction in one direction (oxidation at the anode, reduction at the cathode) are adequate for the desired system discharge rates.

When selecting electrochemical reactions, it is evident that the reactants and products must be compatible with the other system components. For example, a reaction product capable of causing precipitation of the drug which subsequently blocks and insulates the electrode surface would be a detriment to the overall system and process. Changes in electrolyte pH can yield drastic changes in transport characteristics and, at some pH values, damage to the skin could occur. In addition, control of the ionic strength of the donor electrolyte can also be very important. Both electromigration and electroosmosis processes are highly dependent on the composition of the electrolyte.

Although systems could be designed which isolate electrochemical reactants and products from the skin, it is most desirable to select constituents that are biocompatible and thus neither irritating nor sensitizing. By comparison of the electrochemical series with a list of biocompatible materials, it can be seen that there are many electrochemical systems which meet this criteria.

This invention also contemplates those situations where the electrochemical reactions are not sufficient to drive the system and the system is supplemented with an integral power source 36 positioned between the donor electrode 10 and the counter electrode 12, as is shown in FIG. 2. An example of a suitable power source is one or more batteries in series, such as 3 volt lithium batteries. By utilizing an independent power source, the electrodes can be similar metals.

A constant current insures a constant ion flow across the skin, regardless of fluctuations in the impedances associated with other system components. The current level can be controlled by a variety of means. For example, a resistor, in series with the electrotransport cell and battery, having a resistance substantially greater than the overall cell resistance could limit the current to some level, although at the expense of consuming a large portion of the battery's power. The ideal controller would not consume much voltage or power. A much better current source can be made by the use of an appropriate field effect transistor (FET) and a variable resistor. FET current controllers which consume only about 0.5-0.7 volts are commercially available.

While the above describes some very simple approaches to electrical power supply and control for electrotransport systems, clearly the list of more complex systems is essentially endless. For example, controllers could be designed which permit the patient to turn the electrotransport system on and off such as with an on demand medication regimen, or to turn the system on and off at some desired periodicity to match the natural or circadian patterns of the body. A relatively simple controller or microprocessor could control the current as a function of time or could generate complex current waveforms such as pulses or sinusoidal waves. Ultimately, controllers might employ some type of feedback system which would monitor biosignals, provide an assessment of the therapy, and adjust the drug delivery accordingly. A typical example, is the monitoring of the blood sugar level for controlled administration of insulin.

Donor Electrode Pad

FIGS. 1, 2, 4 and 7 illustrate embodiments of the invention where the donor electrode pad 14 is comprised solely of a drug containing reservoir. These systems adhere by means of in-line ion conducting adhesive, a peripheral adhesive or an adhesive overlay. Use of a separate adhesive can be eliminated entirely by selecting a material such that pad 14 is a self-adhering matrix, as is shown in FIG. 5

The donor electrode pad 14 can be a polymeric matrix structure formed by blending drug with an inert polymer by melt blending or solvent casting or extrusion, for example. The drug is preferentially present in a ratio of total blend of about 25 to 90 percent to insure an open pore (microporous) structure in the polymer. Lower drug concentrations may be useful if a delay in release from the system is desired.

Suitable polymers are those which can be blended with the drug in the melt phase. These include, without limitation, polyethylene, polypropylene, polyisoprenes and polyalkenes, polyvinylacetate, ethylene vinyl acetate polymers such as those described in U.S. Pat. No. 4,144,317, incorporated herein by reference, polyamides and polyurethanes. The matrix can also be prepared to include plasticizers in polymers such as polyvinylchloride, cellulose acetate and cellulose acetate butyrate, and blends thereof.

Other suitable polymers are those which dissolve in organic solvents. These include, without limitation, ethylcellulose, cellulose acetate, ethylene vinyl acetate, polyurethane and nylons, and blends thereof.

The matrix can be crosslinked with the drug in place such as a silastic matrix, or the polymers can be prefabricated and sorbed with the drug from solutions as is the case with cellulose, woven fiber pads and sponges.

The donor electrode pad 14 can alternately be a gel matrix structure, formed similarly to the polymeric matrix structure wherein the gel is formed of a hydrophilic polymer which is swellable or soluble in water. Such polymers can be blended with the drug in any ratio, preferably from a few percent up to 50 percent. The polymers can be linear or cross linked and suitable examples include, without limitation, polyethylene oxides, polyox, polyox blended with polyacrylic acid or Carbopol ®, cellulose derivatives such as hydroxypropyl methyl cellulose, hydroxyethyl cellulose, hydroxypropyl cellulose, pectin, starch, guar gum, locust bean gum, and the like, along with blends thereof. This list is merely exemplary of the materials suited for use in this invention. A more extensive list can be found in J.R.Scott & W.J.Roff, Handbook of Common Polymers (CRC Press, 1971).

Supporting electrolytes which are chemically inert and pharmacologically nontoxic, may also be included in the donor electrode pad. The drug itself often acts as a buffer and so the addition of buffers is often not necessary.

The donor electrode pad 14 can also be an ion exchange structure. The rationale for choosing the polymeric counter-ion to the drug is to immobilize the counter-ion. The ion exchange structure can be used to assist in controlling the composition of the electrolyte contained therein and to optimize drug delivery efficiency. For example, as metal ions are released from the electrode surface, rather than accumulating in the drug reservoir and perhaps lowering the drug transport, the metal ions can simply replace and release the drug from the ion exchange structure.

The required thickness of the donor electrode pad 14 can readily be determined from the calculation of the equivalents of drug transported which is given by the following equation:

$$m = [\tau A (MW) t_+ i] / z F$$

where:
m = mass of drug transported
$\tau$ = treatment time
A = drug delivery area
MW = molecular weight of the drug
$t_+$ = transport number of the drug $i_t$ = total current
$z$ = valency of the drug ion For purposes of illustration only, assume a system has the following characteristics: a drug having a molecular weight of 300, an area of 1 cm², a total current of 100 μA/cm², a valency of 1, a transport number of 0.5, a 24 hour treatment time, a membrane density of 1 g/ml and a 50/50 ion exchange resin/polymer matrix loading of 1 meq/mL (ion exchange material resin bed loading of 2 meq/mL), the equivalents of drug transported is as follows:

$$m = (24 \times 60 \times 60)(1)(0.5)(10^{-4})/(1)(96500)$$
$$= 4.48 \times 10^{-5} \text{ equivalents (which corresponds to 13.4 mg)}$$
$$= 45 \text{ μeq}$$

For this amount of drug, the following thickness of ion exchange loaded membrane (donor electrode pad 14) would be required:

(0.045 meq drug) (1 meq/mL membrane loading) = 0.045 mL membrane

For a 1 cm² delivery area, this would correspond to a membrane thickness of about 0.45 mm or 18 mils.

The ion exchange structure can be an ion exchange membrane which is prepared from a prefabricated membrane having the desired ion exchange capacity and conductance. The donor electrode pad 14 is loaded with drug by soaking the ion exchange membrane in a drug solution at a pH where the drug is ionized as well as the resin. Suitable materials for use with this invention are anionic and cationic membranes sold under the trademark Raipore®, by The Electrosynthesis Co., Inc. East Amherst, N.Y. These can provide ion exchange capacities within the range of 0.8–1.5 meq/g and resistances within the range of 0.2–17 ohm-cm² (measured in 0.6N KCl).

Alternately, the ion exchange structure can be a heterogeneous matrix. Donor electrode pad 14 can be fabricated by loading ion exchange resin beads with drug by soaking, as described above. The resin beads can subsequently be compounded into a matrix structure by melt blending the beads with molten polymer matrix and subsequent extrusion. Suitable polymers are those with sufficiently low melting points and include, without limitation, polyethylene, polyalkenes, rubbers, copolymers such as Kraton®, ethylene vinyl acetate, nylons and polyurethanes. The donor electrode pad 14 can also be fabricated by loading the ion exchange beads (containing drug) into a matrix that is subsequently cross linked, similar to silicone rubber. Alternately, the beads can be blended in an organic solvent containing a polymeric binder such as ethylcellulose dissolved in methylene chloride or methanol, or cellulose acetate, polyurethane or rubber dissolved in petroleum ether. Generally, suitable binder polymers are selected from materials having low electrical or ion conductive properties.

Suitable commercially available cation and anion resins include, without limitation, those listed below.

TABLE I

| NAME (Active Charge Group) | FORM | SIZE mesh | DRY meg/g | RESIN BED meg/mL | MOISTURE % of total | PORE SIZE |
|---|---|---|---|---|---|---|
| Cation Exchange Resins | | | | | | |
| AG 50W-X12* (Sulfonic acid) | H | 100–200 | 5 | 2.3 | 42–48 | small |
| Bio-Rex 70* (Carboxylic acid) | Na | 200–200 | 10.2 | 3.3 | 65–74 | large |
| Chelex 100* Chelating resin (Iminodiacetic acid) | Na | 100–200 | 2.9 | 0.7 | 71–76 | large |
| Amberlite IR-120** (Sulfonic acid) | H | 20–50 | 5.0 | 1.8 | 49–55 | medium |
| Anion Exchange Resins | | | | | | |
| AG 1-X8* ($R_4N^+$) | Cl | 20–50 | 3.2 | 1.4 | 39–45 | medium |
| Amberlite IRA-400** ($RN(CH_3)_3^+$) | Cl | 20–50 | 3.3 | 1.2 | 42–48 | medium |

*represents Trademark names of Bio-Rad
represents Trademark names of Mallinckrodt The donor electrode pad 14** can also be fabricated so as to form a self-adhering matrix as is illustrated in FIG. 5. Suitable matrix materials include, without limitation, poly(styrene-butadiene) and poly(styrene-isoprene-styrene) block copolymers, and a high and low molecular weight polyisobutylene copolymers. The matrix may also be of an ethylene vinyl acetate (EVA) copolymer of the type described above. Other suitable self-adhering matrix materials are set forth in the art such as are described in U.S. Pat. Nos. 4,391,278, 4,474,570, and 4,702,732, all of which are incorporated herein by reference.

Adhesive properties are enhanced by adding a resinous tackifier. This is especially important when using a non-tacky polymeric matrix. Example of suitable tackifiers include products sold under the trademarks Staybelite Ester #5 and #10, Regal-Rez and Piccotac, all of Hercules, Inc. of Wilmington, Del. Additionally, the matrix may contain a rheological agent, suitable examples of which include mineral oil and silica.

In addition to the drug and electrolyte, the donor electrode pad may also contain other materials such as dyes, pigments, inert fillers, excipients, and other conventional components of pharmaceutical products or transdermal therapeutic systems known to the art.

Electrodes

The electrode material is selected based upon the electrochemical considerations enumerated above. Numerous electrode configurations are well known in the art; for example, U.S. Pat. Nos. 4,474,570 and 4,557,723, both of which are incorporated herein by reference.

This invention provides a unique configuration whereby the electrodes are in direct contact with each other as in FIG. 1, or with a power source as in FIG. 2. This configuration provides a distinct advantage in manufacturing.

Electrodes 10 and 12 can be metal foils. Alternately, the electrodes can be fabricated by calendering, film evaporation or by embedding the metal powder desired in a binder matrix. For example, zinc powder, silver powder and/or silver chloride powder can be embedded in an ethylene vinylacetate matrix, with the preferred amount of metal being within the range of 30-90 volume percent and the remainder being the binder matrix.

Counter Electrode Pad

Suitable materials for the counter electrode pad 16 are the same as those listed for the donor electrode pad 14. The counter electrode pad may optionally contain drug.

In general, the counter electrode pad will contain an appropriate amount of a suitable redox species and a high concentration of a chemically inert, pharmacologically non-toxic salt such as sodium chloride, alkaline salts, chlorides, sulfates, nitrates, carbonates, phosphates, and organic salts such as ascorbates, citrates, acetates and mixtures thereof. The addition of a buffer is also usually desired. An example of a suitable counter electrode pad composition when the counter electrode is a silver/silver chloride cathode, is an electrolyte containing sodium chloride with a sodium phosphate buffer.

Insulator

The insulator 18 performs the function of preventing ion transport between the electrode pads 14 and 16. It is preferably formed of a non-conducting polymeric material, which is impermeable to both the passage of ions and water. One such suitable material is ethylene vinyl acetate, as is described in detail above. Preferably, the insulating material used, will be the same as the polymer selected for the electrode pads to improve bonding between the different system components.

Backing

The non-conducting backing member 20 serves several functions. It protects the electrodes 10 and 12 from exposure. It prevents leakage of drug or other system components. It also can provide support for the system, where needed. Backing member 20 can be flexible or nonflexible and suitable materials include, without limitation, cellophane, cellulose acetate, ethylcellulose, plasticized vinyl acetate-vinyl chloride copolymers, polyethylene terephthalate, polyethylene terephthalate/ethylene vinyl acetate, nylon, high and low density polyethylene, polypropylene, polyester, polycarbonate, polyurethane or other polyester films, polyvinylidene chloride and coated flexible fibrous backings such as paper and cloth. Such backings can be in the form of precast films or fabrics which are bonded to the electrodes by heat or adhesives or they can be coated onto the electrode.

Manufacture

The donor electrode pad 14 and the counter electrode pad 16 such as is shown in FIG. 4, can be coextruded with a nonconducting polymer as an insulator 18. Pads 14 and 16 and the insulator 18 can all be extruded onto a release liner 28 having a peripheral adhesive layer 24. The donor electrode 10 can then be laminated onto the donor electrode pad 14.

The counter electrode assembly is comprised either solely of the counter electrode 12 as in FIG. 1 or the counter electrode 12 and a power source 36 as in FIG. 2. This assembly is first laminated onto the counter electrode pad 16 and then laminated onto the donor electrode with electrically conductive cement.

The entire system is deposited onto the backing 20 which is a substrate polymer film web, and then cast and packaged.

Having thus generally described our invention, the following examples will illustrate how variations of the above described parameters provide therapeutically effective electrotransport systems.

EXAMPLE I

Figure 9:
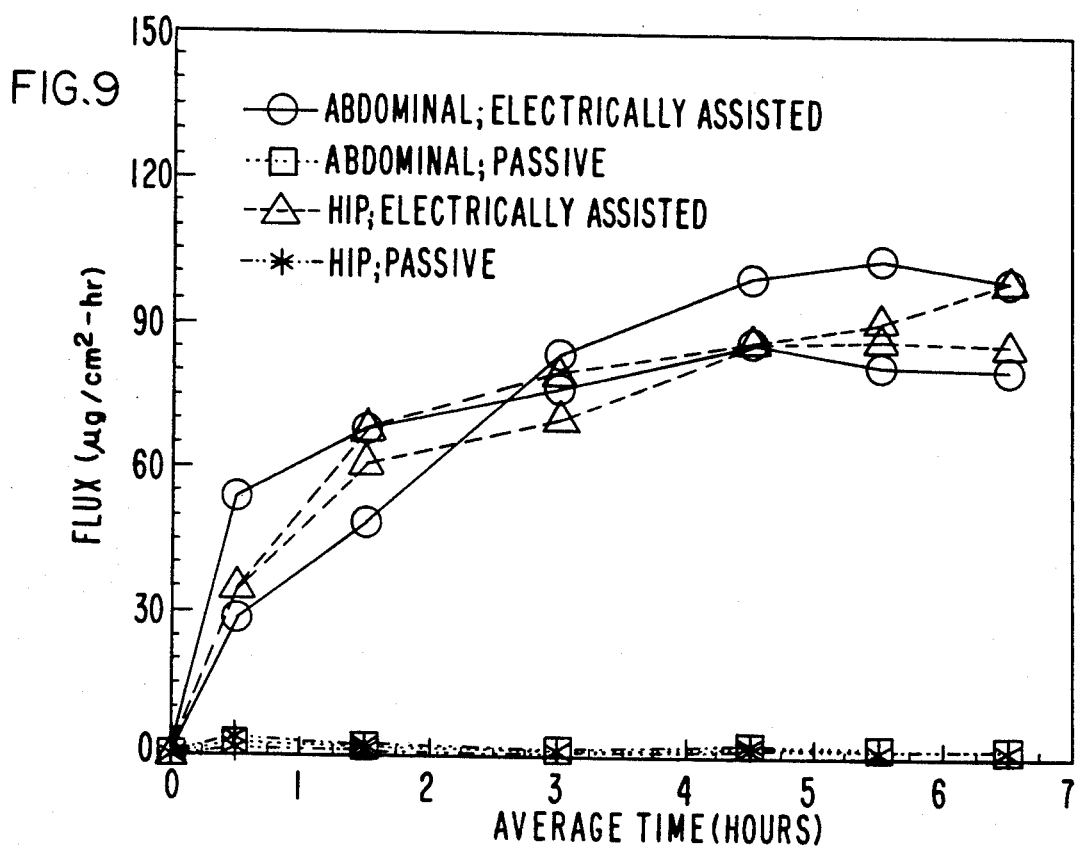
FIG. 9 is a graph illustrating the increase in the metoclopramide hydrochloride flux through human cadaver epidermis, using 0.1 mA/cm$^2$ current (electrically assisted) as opposed to the flux under zero current conditions (passive)

An experiment was performed to show the improved flux attainable using electrotransport principles. The drug tested was metoclopramide HCl which has a molecular weight of 336. In vitro flux data was obtained at 32° C., utilizing abdominal and hip cadaver skin specimens, measuring both the passive (zero current density) and the active (100 $\mu$A/cm$^2$ current density) fluxes. The donor medium was aqueous having a drug concentration of 0.092 g/ml and the receptor solution was normal saline. The polarity of the system was anodic. The test data obtained is presented graphically in FIG. 9 where the metoclopramide HCl flux ($\mu$g/cm$^2$-hr) is plotted against average time (hours). The passive flux of this drug is about a factor of 20 smaller than the active flux values which are within the range of 80-105 $\mu$g/cm$^2$-hr at steady state.

EXAMPLE II

Prototype donor electrode pads were fabricated using a variety of different reservoir materials: cation exchange and microporous (PVA and EVA 40) membranes and gels (HEC and HPC). The donor electrode was silver foil. The composition was 50 dry weight percent reservoir material and 50 weight percent metoclopramide hydrochloride. The laminated structure was as follows:

Backing/Ag/Polymer, Metoclopramide HCl/TYVEC

These prototypes yielded in vitro transport rates across skin, comparable to those obtained using liquid electrolyte donor reservoirs; i.e., in the range of about 70 $\mu$g/cm$^2$-hr. Full scale systems according to this invention are thus capable of delivering metoclopramide at levels within the range of 10-30 mg/day, which is the therapeutic rate necessary for treatment of nausea and vomiting. It is also expected that the systems according to this invention will be capable of delivering 140 mg/day of metoclopramide for the treatment of emesis induced by chemotherapy.

EXAMPLE III

Figure 10:
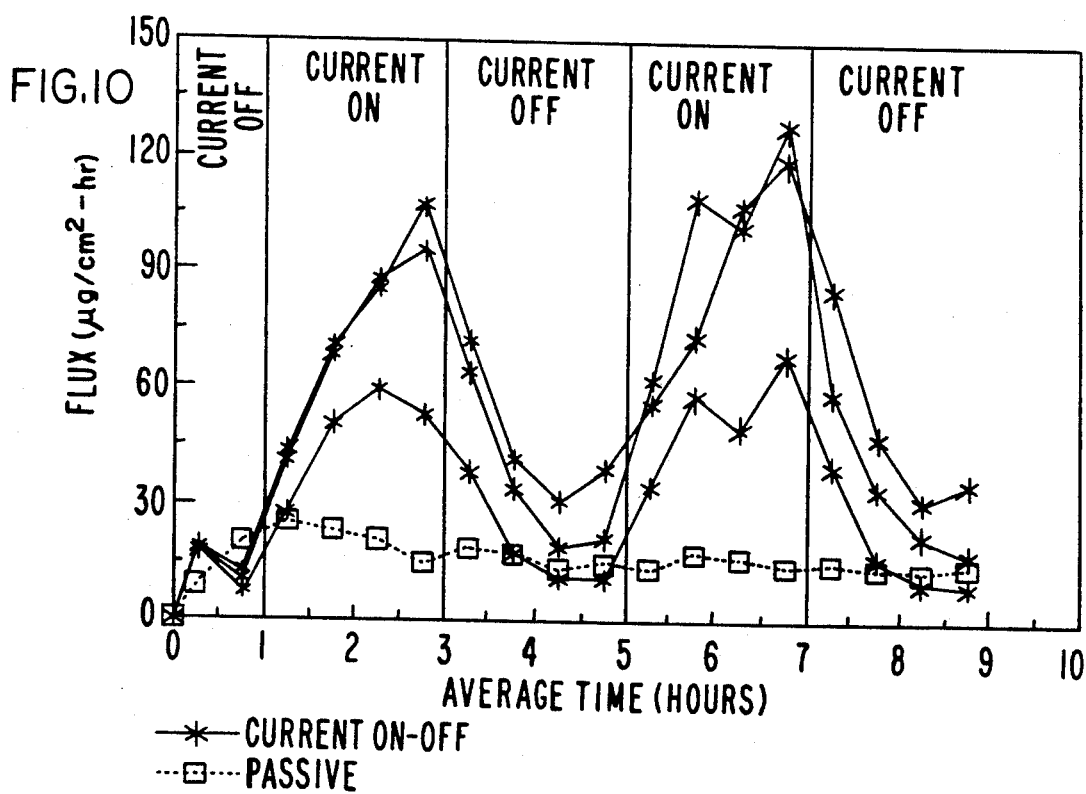
FIG. 10 illustrates the on-off capability of the electrotransport systems of this invention.

The capability of using the electrotransport systems of this invention to provide for patterned delivery was demonstrated. As is shown in FIG. 10, metoclopramide transport from a PVA reservoir across human epidermis can be turned on and off by controlling the applied electrical current. During the intervals when current was "on", the applied electrical current was 100

μA/cm². Each curve was obtained using a separate skin specimen and one cell (dotted line) was run in the passive mode for the entire experiment. The response time is on the order of one hour for the type of skin specimen used, namely heat-stripped human epidermis.

EXAMPLE IV

It was demonstrated that an electrotransport system according to this invention which incorporates an appropriate galvanic redox couple could provide sufficient voltage to drive the desired current. Utilizing metoclopramide HCl in the donor electrode compartment, saline as the receptor solution and saline in the counter electrode compartment, along with a Zn anode with a Ag/AgCl cathode, the test cells (system) had the following layout:

Zn/Metoclopramide
HCl/Skin/Saline/Skin/Saline/Ag/AgCl

Figure 11:
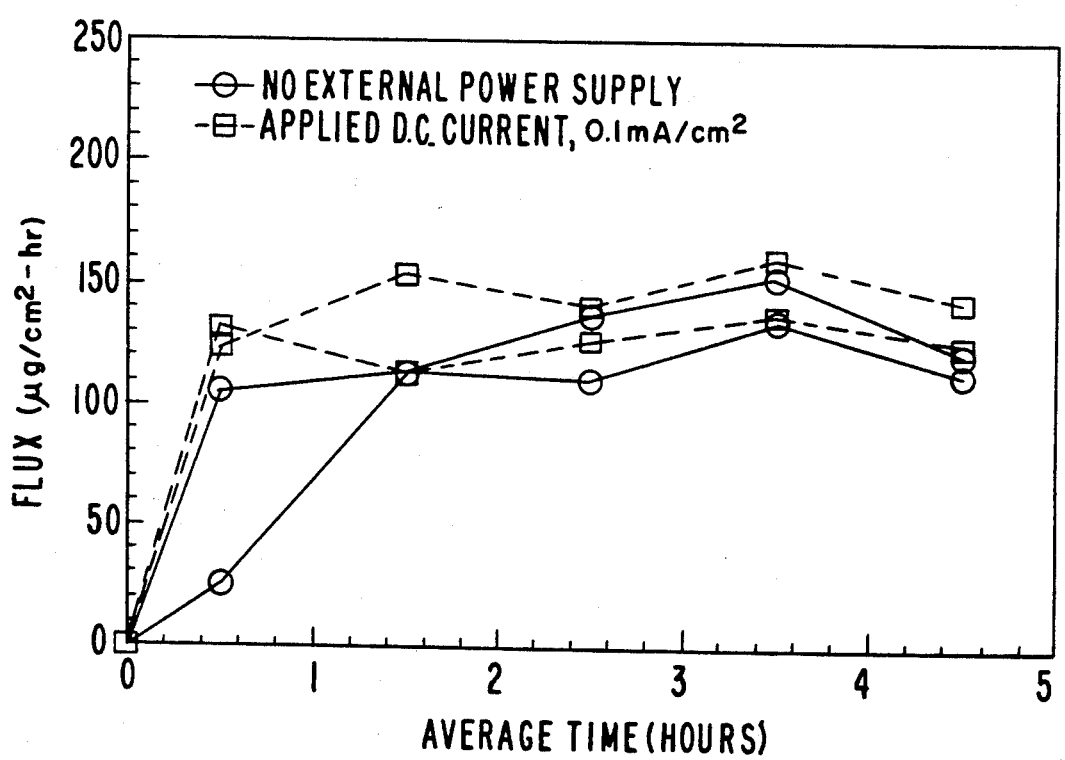
FIG. 11 illustrates the drug flux attainable with a galvanic couple versus an external power supply.

The in vitro transport of metoclopramide across human epidermis from four systems was compared. Two systems operated solely on the galvanic couple (no external power supply) and the other two systems had an applied DC current of 100 μA/cm². As is shown in FIG. 11, the metoclopramide flux from the galvanic powered systems was approximately the same as that obtained from systems having the current controlled by an external device. This demonstrates that an inexpensive device could be made according to this invention, without the need for incorporating a separate power source or battery, and depending upon the desired performance characteristics, without any electronic components for controlling the electrical current.

EXAMPLE V

One embodiment of an electrotransport transdermal system according to this invention would have the configuration illustrated in FIG. 1 and would be made of the following materials. The donor electrode pad 14 would be 50 dry weight percent EVA 40 and 50 wt % metoclopramide HCl, while the counter electrode pad 16 would be 50 dry weight percent EVA 40 with the balance being NaCl and sodium phosphate. To form a galvanic couple capable of supplying enough power to run the system, the donor electrode 10 would be Zn while the counter electrode 12 would be Ag/AgCl. Insulator 18 would be EVA-40 and backing member 20 would be polyethylene terephthalate/EVA. The system would remain in position by peripheral adhesive 24 made of polyisobutylene and mineral oil.

EXAMPLE VI

Another embodiment of an electrotransport transdermal system according to this invention would have the configuration illustrated in FIG. 2 and would be made of the following materials. The donor electrode pad 14 and counter electrode pad 16 would have the same composition as that in Example V. The donor electrode 10 would be Ag while the counter electrode 12 would be Ag/AgCl, and positioned between them would be a 0.3 volt lithium battery acting as the power source 36. Insulator 18 and backing member 20 would be of the same materials as in Example V. The system would remain in position by an adhesive overlay 26 made of polyisobutylene and mineral oil.

EXAMPLE VII

Another embodiment of an electrotransport transdermal system according to this invention would have the configuration illustrated in FIG. 5 and would be made of the following materials. The first electrode pad 14 would be a self-adhering karaya gum composition containing l-dopa formulated at a pH about 3.5 below the isoelectric point. The second electrode pad 16 would also be a self-adhering karaya gum composition containing l-dopa formulated at a pH of about 7.5 above the isoelectric point. In this manner, both electrode pads act as donors and deliver agent to the body surface. To form a galvanic couple capable of supplying enough power to run the system, the donor electrode 10 would be Zn while the counter electrode 12 would be Ag/AgCl. Insulator 18 would be EVA 40 and backing member 20 would be polyethylene terephthalate/EVA.

Having thus generally described our invention and described in detail certain preferred embodiments thereof, it will be readily apparent that various modifications to the invention may be made by workers skilled in the art without departing from the scope of this invention and which is limited only by the following claims.

What is claimed is:

1. An electrotransport device for delivering a beneficial agent in the form of a water soluble salt through a body surface, comprising:

A donor electrode electrically connected to a donor electrode pad containing the beneficial agent to be delivered, the donor electrode pad being positioned in beneficial agent ion transmitting relationship to said body surface;

a counter electrode electrically connected to a counter electrode pad containing a water soluble electrolyte salt, the counter electrode pad being positioned in electrolyte salt ion transmitting relationship to said body surface at a location spaced apart from the donor electrode pad;

a source of electrical power electrically connected to the donor and counter electrodes;

wherein the donor electrode pad comprises a hydrophobic polymer matrix which is substantially free of any hydrophilic polymer, the hydrophobic polymer matrix containing the water soluble beneficial agent salt blended therein, the beneficial agent salt being present as about 25 to 90 weight % of the total blend of the reservoir and the agent, the blended beneficial agent salt creating a microporous structure in the hydrophobic polymer matrix.

2. The device of claim 1, wherein the hydrophobic polymer comprises an ethylene vinyl acetate copolymer.

3. The device of claim 1, wherein the hydrophobic polymer comprises a polyalkene.

4. The device of claim 1, wherein the hydrophobic polymer comprises a polyisobutylene copolymer.

5. The device of claim 1, wherein the hydrophobic polymer comprises a mixture of a high molecular weight polyiosbutylene copolymer and a low molecular weight polyisobutylene copolymer.

6. The device of claim 1, wherein the donor electrode pad contains about 50 wt % of the beneficial agent on a dry weight basis.

7. The device of claim 1, wherein the donor electrode pad comprises a self-adhering matrix.

8. The device of claim 1, wherein the donor electrode pad also contains a resinous tackifier.

9. The device of claim 1, including a layer of an ion transmitting adhesive on a skin facing side of the donor electrode pad.

10. The device of claim 1, wherein the source of electrical power comprises a battery.

11. The device of claim 10, wherein the source of electrical power applies an electrical current density of about 100 $\mu A/cm^2$.

12. The device of claim 1, wherein the donor electrode comprises a metal foil.

13. The device of claim 1, wherein the donor electrode comprises an electrochemically oxidizable or reducible powdered material in a binder matrix.

14. The device of claim 13, wherein the electrochemically oxidizable or reducible powdered material is selected from the group consisting of silver powder, zinc powder, and silver chloride powder.

15. The device of claim 1, wherein the beneficial agent salt comprises a drug.

16. The device of claim 15, wherein the drug comprises metoclopramide.

17. The device of claim 15, wherein the drug comprises a peptide.

18. The device of claim 15, wherein the drug comprises a protein.

* * * * *